US008900863B2

(12) United States Patent
Kallis et al.

(10) Patent No.: US 8,900,863 B2
(45) Date of Patent: Dec. 2, 2014

(54) METHODS FOR ISOLATING MONONUCLEAR CELLS THAT INCLUDE A SUBPOPULATION OF MESENCHYMAL PROGENITOR CELLS AND VASCULAR CELLS THAT INCLUDE A SUBPOPULATION OF ENDOTHELIAL PROGENITOR CELLS FROM UMBILICAL CORD TISSUE

(75) Inventors: Zacharias Kallis, Nicosia (CY); Kyriacos Matsis, Strovolos (CY)

(73) Assignee: Lifeline Cord Blood Bank, Strovolos Nicosia (CY)

( * ) Notice: Subject to any disclaimer, the term of this patent is extended or adjusted under 35 U.S.C. 154(b) by 173 days.

(21) Appl. No.: 12/972,118

(22) Filed: Dec. 17, 2010

(65) Prior Publication Data

US 2011/0151556 A1 Jun. 23, 2011

Related U.S. Application Data

(60) Provisional application No. 61/288,211, filed on Dec. 18, 2009.

(51) Int. Cl.
| | | |
|---|---|---|
| *C12N 5/077* | (2010.01) | |
| *C12N 5/071* | (2010.01) | |
| *C12N 5/0775* | (2010.01) | |
| *A61K 35/44* | (2006.01) | |
| *C12N 5/073* | (2010.01) | |
| *C12M 1/26* | (2006.01) | |

(52) U.S. Cl.
CPC ............ *C12N 5/0668* (2013.01); *C12N 5/0692* (2013.01); *A61K 35/44* (2013.01); *C12N 5/0605* (2013.01)
USPC .......................................... 435/374; 435/366

(58) Field of Classification Search
CPC ..... C12N 5/0605; C12N 5/0668; C12N 5/092
USPC .................................................. 435/366, 374
See application file for complete search history.

(56) References Cited

U.S. PATENT DOCUMENTS

2008/0118477 A1* 5/2008 Christopherson ............ 424/93.7

FOREIGN PATENT DOCUMENTS

WO WO 2008/060037 A1 5/2008

OTHER PUBLICATIONS

Friedman et al.; Umbilical Cord Mesenchymal Stem Cells: Adjuvants for Human Cell Transplantation; Biology of Blood and Marrow Transplantation; vol. 13; No. 12; pp. 1477-1486; Dec. 2007.*
Schallmoser et al.; Rapid Large-Scale Expansion of Functional Mesenchymal Stem Cells from Unmanipulated Bone Marrow Without Animal Serum; vol. 14; No. 3; pp. 185-196; Sep. 2008.*
Can et al.; Concise Review: Human Umbilical Cord Stroma with Regard to the Source of Fetus-Derived Stem Cells; Stemcells; vol. 25, pp. 2886-2895 (2007).*
LabOnline; Automated gentle tissue dissociator; http://www.labonline.com.au/products/26724-Automated-gentle-tissue-dissociator; posted online Sep. 8, 2008.*
Kadem et al.: "Simultaneous isolation of vascular endothelial cells and mesenchymal stem cells from the human umbilical cord"; In Vitro Cellular & Developmental Biology—Animal Feb. 2009, vol. 45, Issue 1-2, pp. 23-27, Abstract.
Seshareckly, Klran et al.: "Method to Isolate Mesenchymal-Like Cells from Wharton's Jelly of Umbilical Cord"; Methods in Cell Biology, vol. 86, 2008, pp. 101-119 Stern Cell Culture. Abstract.

\* cited by examiner

*Primary Examiner* — Jim Ketter
*Assistant Examiner* — Antonio Galisteo Gonzalez
(74) *Attorney, Agent, or Firm* — DLA Piper LLP (US)

(57) ABSTRACT

Provided herein are methods and kits for the isolation, processing and cryopreservation of mesenchymal cells from the Wharton's Jelly and vascular progenitor cells from umbilical cord tissue. Also provided are isolated mesenchymal cells or vascular progenitor cells obtained by the invention methods, and compositions thereof.

7 Claims, 1 Drawing Sheet

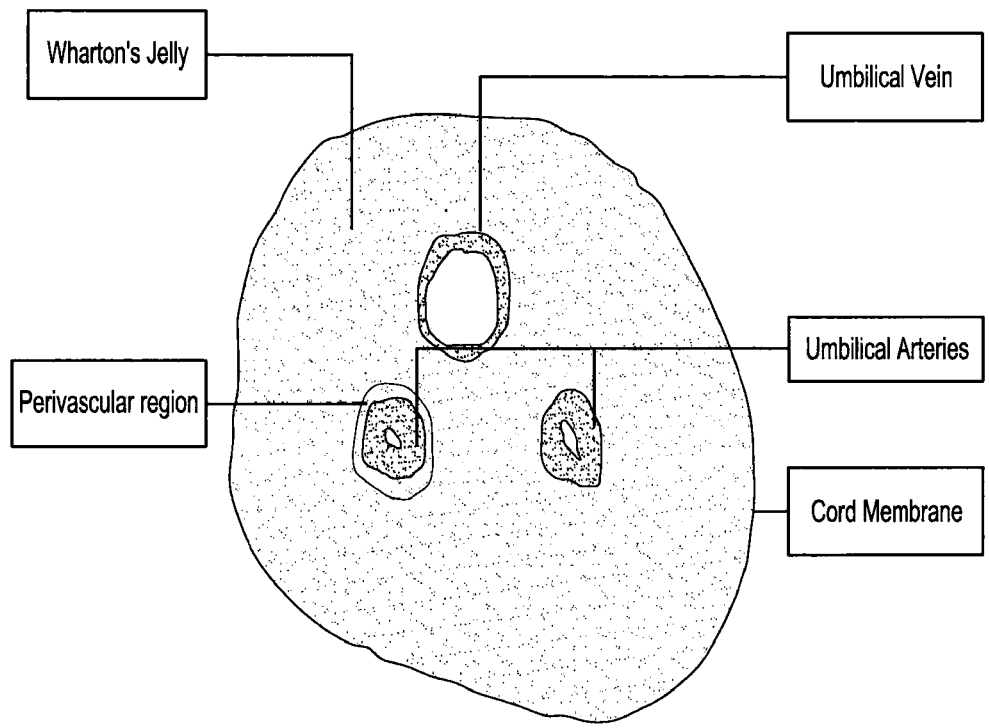

METHODS FOR ISOLATING MONONUCLEAR CELLS THAT INCLUDE A SUBPOPULATION OF MESENCHYMAL PROGENITOR CELLS AND VASCULAR CELLS THAT INCLUDE A SUBPOPULATION OF ENDOTHELIAL PROGENITOR CELLS FROM UMBILICAL CORD TISSUE

CROSS REFERENCE TO RELATED APPLICATION(S)

This application claims the benefit of priority under 35 U.S.C. §119(e) of U.S. Ser. No. 61/288,211, filed Dec. 18, 2009, the entire content of which is incorporated herein by reference.

BACKGROUND OF THE INVENTION

1. Field of the Invention

The invention relates generally to mesenchymal cells and endothelial progenitor cells, and more specifically to methods for the isolation of mesenchymal cells and vascular progenitor cells from umbilical cord tissue.

2. Background Information

It has already been established that an excellent source for Mesenchymal Stromal or progenitor or stem cells is the Wharton's jelly which is the stroma of the umbilical cord. The umbilical cord originates from the extraembryonic mesoderm at day 13 of embryonic development, and is composed of two arteries and one vein, all of which are surrounded by the Wharton's Jelly which is a unique connective tissue stroma rich in proteoglycans and mucopolysaccharides. These stromal cells embedded in the collagen-rich matrix are myofibroblasts rather than typical fibroblasts. In recent studies, cord stromal cells were reported to possess mesenchymal stem cell character with, the differentiation of umbilical cord stromal cells into mesenchymal cell lineages, such as cardiomyogenic, chondrogenic, osteogenic, and adipogenic types. The isolation, culturing, and differentiation behavior of human perivascular umbilical cells and obtained osteogenic nodules has already been demonstrated by several researchers. The differentiation capacity of human umbilical cord mesenchymal stem cells into dopaminergic neurons has also been demonstrated. Most recently, some of embryonic stem cell markers, such as Oct-4, Sox-2, and Nanog, were demonstrated in porcine umbilical cord matrix cells. Similarly, endothelial progenitor cells obtained from the vascular system of the umbilical cord have been shown to possess the properties of similar progenitor cells obtained from other sources.

Mesenchymal stromal cells (MSCs), as defined by the International Society for Cellular Therapy, are plastic-adherent cells with a specific surface phenotype and have the capacity to proliferate (self-renew) and to differentiate into various lineages including bone, cartilage, adipose. Such cells can be derived from several different sources, such as trabecular bone, adipose tissue, synovium, skeletal muscle, dermis, pericytes, blood, and bone marrow. MSCs derived from bone marrow and adipose tissue have been studied extensively. MSCs derived from bone marrow can be differentiated into bone, cartilage, tendon, muscle, adipose tissue, and hematopoietic cell-supporting stroma. Thus, they are candidates to treat patients suffering from bone disorders, heart failure, etc. Because MSCs can be isolated from adults in significant number, they have been examined closely for therapeutic utility. For example, MSCs support the ex vivo expansion of hematopoietic stem cells, act as immune modulators, release cytokines and growth factors, and they home to sites of pathology. A significant number of trials are ongoing using bone marrow-derived MSCs for a variety of indications, for example, acute myocardial infarction, stroke, and graft versus host disease. Nevertheless, there are limitations associated with MSCs derived from bone marrow for cell-based therapy. For example, collection of MSCs from bone marrow is an invasive and painful procedure. In normal aging, the marrow cavity fills with yellow fat. Thus, there may be difficulty in obtaining MSCs from older individuals. Along these lines, differences have been found between bone marrow-derived MSCs collected from a fetus versus adult-derived MSCs. For example, fetal MSCs have a longer life in vitro compared to adult-derived MSCs and MSCs derived from adults have a useful lifespan in vitro of about five passages.

Researchers have demonstrated that cells derived from the Wharton's Jelly in umbilical cords (so called umbilical cord matrix cells or UCMSCs) have properties of MSCs. While UCMSCs have surface phenotype, differentiation capability, and immune properties similar to MSCs derived from bone marrow and adipose, UCMSCs are more similar to fetal MSCs in terms of their in vitro expansion potential. In contrast to bone marrow- and adipose-derived MSCs, UCMSCs are isolated from the umbilical cord following birth and may be collected following either normal vaginal delivery or caesarean section. UCMSCs are easily expandable in vitro, and may be cryogenically stored, thawed, and reanimated. UCMSCs grow as plastic-adherent cells, express a surface phenotype similar to other MSCs, and differentiate into multiple lineages. Umbilical cord matrix cells have been safely transplanted and ameliorated symptoms in an animal model of Parkinson's disease, neural damage associated with cardiac arrest/resuscitation, retinal disease, and cerebral global ischemia.

Umbilical Cord MSCs. MSCs have been isolated from several compartments of the umbilical cord (FIG. 1). Specifically, the MSCs have been isolated from umbilical cord blood, umbilical vein subendothelium, and the Wharton's jelly (FIG. 1). Within Wharton's jelly, MSCs have been isolated from three relatively indistinct regions: the perivascular zone, the intervascular zone, and the subamnion. It is unknown whether MSCs isolated from the different compartments of the umbilical cord represent different populations. This discussion is confined to the MSCs isolated from Wharton's jelly cells (WJCs; zones 3-5 in FIG. 1). A sub-population of the Wharton's Jelly cells (WJC) display MSC surface markers, suggesting that they are of the MSC family.

WJCs have stromal support properties deriving from the early stages of embryogenesis as extraembryonic mesenchyme, that is, primitive Wharton's jelly, surrounding the migrating embryonic blood island cells during their migration to the aorta-gonad mesonephros (AGM) from the yolk sac region. WJCs retain this property as demonstrated by their role in ex vivo hematopoietic expansion and in vivo engraftment of HSCs. It has been reported that WJCs produced cytokines similar to those of BMSCs and that WJCs synthesized granulocyte macrophage colony stimulating factors (GM-CSF) and granulocyte colony stimulating factors (G-CSF) that BMSCs did not. WJCs differ from BMSCs because WJCs are slower to differentiate to adipocytes. Since this and other features (listed below) are shared with MSCs derived from umbilical cord blood (UCB), it is unclear whether the MSCs derived from UCB differ from those found in Wharton's jelly. UCB-MSCs and WJCs have several common properties, such as poor ability to differentiate to adipocytes, shorter doubling times than BMSCs, and greater numbers of passages to senescence. Like WJCs, UCB-MSCs may make GM-CSF, although this has not been consistently found. It is clear that HSCs can be expanded by MSCs from both UCB and WJC (FIG. 1).

Compartments within the umbilical cord. Five separate regions have been shown to contain mesenchymal stromal cells: (1) MSCs can be isolated from 20-50% of freshly prepared mononuclear cell fractions from umbilical cord blood; (2) MSCs have been isolated from umbilical vein subendothelial layer; (3) MSCs can be isolated following enzymatic digestion of the outer layers of umbilical vessels, for example, the perivascular region; (4) intravascular space consistently produces MSCs in healthy individuals; (5) the subamnion region. Wharton's jelly includes zones 3 through 5. This review focuses on Wharton's jelly-derived cells and not on MSCs derived from umbilical cord blood (zone 1) or umbilical vein subendothelium (zone 2).

There are differences between BMSCs, UCB-MSCs and WJCs. First, the isolation frequency of colony forming units (CFU)-F from bone marrow is estimated to be in the range of 1-10 CFU-F per $10^6$ mononuclear cells (MNCs) and in umbilical cord blood is reported to be around one CFU-F clone per 108 MNCs to 1-3 CFU-F per 106 MNCs. [Note: The isolation frequency from first semester foetal blood-derived MSCs was 8.2 CFU-F per $10^6$ MNCs]. In contrast, cells derived from Wharton's jelly have a higher frequency of CFU-F. Thus, an order of magnitude more of MSCs than of Wharton's Jelly-Derived Stromal Cells bone marrow or umbilical cord blood may be found in the initial isolation from WJ. Second, coupled with the greater CFU-F frequency, the doubling time of WJCs and UCB-MSCs is shorter than adult bone marrow-derived MSC (BMSCs). Faster doubling time is a common feature for MSCs derived from foetal blood, cord blood, and Wharton's jelly, and this common feature is thought to reflect the relatively primitive nature of these MSCs compared to adult BMSCs. An important difference between UCB-MSCs and WJCs is that WJCs can be isolated from close to 100% of the samples, even from umbilical cords that are delayed in their processing up to 48-hour.

Wharton's jelly cells, like bone marrow stromal cells and other mesenchymal cells, are plastic adherent, stained positively for markers of the mesenchymal cells such as CD10, CD13, CD29, CD44, CD90, and CD105 and negatively for markers of the hematopoietic lineage. Moreover, WJCs morphologically resemble MSCs and can be expanded more than bone-marrow derived MSCs in culture. Human WJCs express precursor cell markers such as nestin. WJCs can be induced to form adipose tissue, bone, cartilage, skeletal muscle cells, cardiomyocyte-like cells, and neural cells and are amenable to biomedical engineering applications. Therefore, these cells fit into the category of primitive stromal cells; and, because Wharton's jelly is a plentiful and inexpensive source of cells, it appears to potentially impact fields such as regenerative medicine, biotechnology, and agriculture. Further work is needed to determine whether WJCs engraft long-term and display self-renewal and multipotency in vivo and, as such, demonstrate that WJCs are a true stem cell population.

SUMMARY OF THE INVENTION

The present invention relates to a method and a dedicated kit for isolation, processing and cryopreservation of mononuclear cells that contain a sub-population mesenchymal stem cells from the Wharton's Jelly and vascular cells that contain a subpopulation of endothelial progenitor cells from umbilical cord tissue.

In one embodiment of the invention, there are provide methods of isolating different cell types from umbilical cord tissue. The method involves separating vascular tissue from Wharton's jelly (WJ) matrix from a sample of umbilical cord; dissociating the tissue and separating dissociated cells from undissociated cells and matrix; and cryopreserving the separated dissociated cells, thereby isolating a cell population that contains mesenchymal cells from umbilical tissue.

In another embodiment of the invention, there are provide methods of isolating vascular progenitor cells from umbilical cord tissue. The method involves separating vascular tissue from Wharton's jelly (WJ) matrix from a sample of umbilical cord; dissociating vascular progenitor cells from the vascular tissue and suspending in plasma; and cryopreserving the dissociated cells, thereby isolating vascular progenitor cells from umbilical tissue.

In another embodiment of the invention, there are provided mesenchymal cells and vascular progenitor cells obtained by the methods provided herein.

In a further embodiment, there are provided cellular therapy products. In one aspect there is provided a composition enriched in mesenchymal progenitor cells. In another aspect, there is provided a composition enriched in vascular progenitor cells. One or the other or both aspects may complement an umbilical cord blood haematopoietic cellular therapy composition or have a medical application as separate cellular therapy products In still another embodiment of the invention, there are provided kits for procuring umbilical cord tissue. The kit includes a sterile container for packing at procurement, 2 sterile clamps to be used on the procurement product during transportation, sterile gauze, alcohol swab or wipe, sterile disposable scissors and saline solution as transportation medium. A temperature data logger is included for temperature monitoring. The kit is contained in a thermally insulated container confining to International Regulations for the transportation of biological material and preserves the integrity of the transported biological material (procurement product).

BRIEF DESCRIPTION OF THE DRAWINGS

FIG. 1 shows a schematic of the umbilical cord compartments.

DETAILED DESCRIPTION OF THE INVENTION

Before the present composition, methods, and culturing methodologies are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Any methods and materials similar or equivalent to those described herein can be used in the practice or testing of the invention, as it will be understood that modifications and variations are encompassed within the spirit and scope of the instant disclosure.

Provided herein is an approach that cryopreserves a product that is retained in its purest form and may be expanded prior to application as well as allowing the possibility to be suitable for direct application without culture in vitro or applied in tissue engineering techniques or gene therapy protocols prior to a therapeutic/medical application.

The methods provided herein allow minimal manipulation and avoidance of expanding the cells in tissue culture techniques for the following reasons. For example, the availability of suitable serum-free growth media is limited and carries a high cost. Animal based sera containing growth media carry the risk of prion or viral contamination thus neither complies with cellular therapy products standards nor GMP techniques for the production of a medical grade cellular therapy product. Cell culture in own plasma is known to cause morphological changes and does not allow proper cell expansion. Risk of contamination during culturing will mean the destruction and loss of such product with financial (and possibly ethical) consequences. Cell culture derived products require 7-21 days which will affect the flow of work and the logistics of in-parallel banking with cord blood and provide possible compromise in traceability and mix-up risk since several cultures are performed all at different stages of growth.

As used herein, the term "sample" refers to any sample suitable for the methods provided by the present invention. The sample can be any sample that may include umbilical tissue or cord. A sample, for example, from a human subject, can be obtained using well known and routine clinical methods (for example, a biopsy procedure).

In one embodiment of the invention, there are provide methods of isolating different cell types from umbilical cord tissue, such as mesenchymal cells. The method involves separating vascular tissue from Wharton's jelly (WJ) matrix from a sample of umbilical cord; dissociating the tissue and separating dissociated cells from undissociated cells and matrix; and cryopreserving the separated dissociated cells, thereby isolating a cell population that contains mesenchymal cells from umbilical tissue.

In another embodiment of the invention, there are provide methods of isolating vascular progenitor cells from umbilical cord tissue. The method involves separating vascular tissue from Wharton's jelly (WJ) matrix from a sample of umbilical cord; dissociating vascular progenitor cells from the vascular tissue and suspending in plasma; and cryopreserving the dissociated cells, thereby isolating vascular progenitor cells from umbilical tissue.

In particular there are provided methods of isolating vascular progenitor cells from the vascular tissue of umbilical cord. In some embodiments the methods incorporates Good Manufacturing Practice (GMP) techniques and the final product complies with International Cellular Therapy Product Standards.

"Progenitor cell" refers to a parent cell that gives rise to a distinct cell lineage by a series of cell divisions.

"Differentiated cell" refers to a non-embryonic cell that possesses a particular differentiated, i.e., non-embryonic, state. The three earliest differentiated cell types are endoderm, mesoderm, and ectoderm.

"Isolating" or "separating" or "dissociating" refers to the process of separating cell aggregates, such as by physical force or chemical treatment. In some embodiments, dissociation may be accomplished by mechanical dissociation which would exclude the use of enzymes (or other cell cleavage products) which might contain non-human materials.

One skilled in the art would understand that dissociation of tissue and cells may be performed by manual or automated dissociation. In one embodiment, dissociation is performed by automated dissociation using a tissue dissociator, such as the gentleMACS™ Dissociator market by Miltenyi Biotec. The dissociated sample may subsequently be disposed through a sieve to further dissociate the tissue and separate the dissociated cells from matrix. In one embodiment the sample is disposed through a sieve from about 1, 2, 3, 4, 5, 6, 7, 8, 9, 10 or more times.

In various embodiments, a single cell suspension is generated from the dissociated tissue. For example, after dissociation, the dissociated cells may be suspended in a fluid, such as plasma, to form the single cell suspension.

In various embodiments, plasma used to provide the single cell suspension is plasma, which is autologous plasma. For example, the plasma used is from the same individual as that of the dissociated cells. This is in contrast to xenotransplantation (from other species) and allotransplantation (from other individual of same species) procedures in which "non-self" components are introduced.

Cryopreservation may be performed by a variety of methods as known in the art. In one embodiment, an instrument is utilized to all for automated mixing and cooling so as to provide controlled and reproducible preparation of cells for cryopreservation. For example, method may utilize the Biosafe Coolmix™ instrument.

In various embodiments, the dissociated cells are cryopreserved using a suitable cryopreservation solution or cryoprotectant. A number of such solutions are known in the art and are suitable for use with the present methods. As used herein, "cryopreservation solution" or "cryoprotectant" refers to a solution or agent containing one or more types of substances which permeate a cell membrane and protect a cell in freezing. Such substances may include glycerol, propylene glycol, dimethyl sulfoxide (DMSO), ethylene glycol, butanediol, and the like. The cryopreservation solution or cryoprotectant may also include one or more substances which do not permeate a cell membrane and protect a cell in freezing including dextran, sucrose, trehalose, percoll, polyethylene glycol, polyvinyl pyrrolidone, bovine serum albumin, ficol, and the like. In one embodiment, the cryoprotectant is a mixture of DMSO and dextran.

In various embodiments, the cryoprotectant is added to the dissociated cells that have been suspended in plasma before the sample is frozen. The cells may be frozen and stored in a cryostorage location in a liquid nitrogen vessel or the like. To ensure that the cell sample is contaminant free, a sample of the final cell suspension including the cryoprotectant may be cultured to determine anaerobic or aerobic contamination.

In another embodiment of the invention, there are provided mesenchymal cells and vascular progenitor cells obtained by the methods provided herein. Accordingly, an enriched sample including mesenchymal cells or vascular progenitor cells is intended to mean a sample in which the sample has been processed as described herein to increase and/or purify the relative population of such cells as compared to if the sample had not been processed, for example, relative to an unprocessed tissue sample. For example, the relative population of cells in a sample may be increased and/or purified by at least about 10%, 25%, 50%, 75%, 100% or by a factor of at least 2, 5, 10, 20, 30, 40, 50, 60, 70, 80, 90, 100, or even 200 as compared to unprocessed tissue. In an exemplary aspect, a sample is produced in which the cells remain intact and/or unlysed and are increased and/or purified by at least about 10%, 25%, 50%, 75%, 100% or by a factor of at least 2, 5, 10, 20, 30, 40, 50, 60, 70, 80, 90, 100, or even 200.

The total number of cells in a processed sample is dependent, in part, on the initial amount of tissue utilized as well as the amount of plasma used to form the suspension. In various aspects, use of a wide range of initial tissue amount is intended as well as plasma volume. Accordingly, in one embodiment, a composition of processed cells includes greater than about 1, 100, 1000, 10,000, 100,000 or 1,000,000 cells per 1 ml of sample.

The present disclosure further provides a kit for use by medical service providers (doctors/gynecologists/obstetricians/midwives) with appropriate equipment for the procurement of umbilical cord sections. In one embodiment the kit contains: a sterile container for packing at procurement (for example, Sterilin product code 190 DB/IRR sterile 250 container is used); 2 sterile clamps fixed at either end of the cord at procurement; sterile gauze for cleaning off fluid (for example, blood/amniotic fluid/vaginal fluid); alcohol/70% ethanol or similar pre-packed swab for decontamination prior to packing; saline (for example, about 100 ml) for irrigation/injection (for example, medical grade 0.9% NaCl solution) to be added to the cord whilst in transit; and disposable sterile scissors. All components suitable for human use/application.

The following examples are intended to illustrate but not limit the invention.

EXAMPLE 1

Generation of Cryopreserved Cells

The methods for isolating mesenchymal and vascular progenitor cells may be conducted as follows and with the following reagents, equipment and consumables.

Medical service providers (doctors/gynecologists/obstetricians/midwives) are provided with appropriate equipment for the collection of umbilical cord sections. The kit may contain:
  i. a sterile container for packing at procurement (for example, Sterilin product code 190 DB/IRR sterile 250 ml container);
  ii. 2 sterile clamps fixed at either end of the cord at procurement;
  iii. sterile gauze for cleaning off fluid (for example, blood/amniotic fluid/vaginal fluid);
  iv. alcohol/70% ethanol or similar pre-packed swab for decontamination prior to packing;
  v. saline for irrigation/injection (for example 100 ml medical grade 0.9% NaCl solution to be added to the cord whilst in transit); and
  vi. sterile scissors (preferably disposable).

Reagents, Consumables and Equipment

Reagents, consumables and equipment may include the following as shown in Table 1.

TABLE 1

Sterile Dissection Kit - Includes fine scissors, mosquito clamp, fine tweezers, and rat tooth clamps (2).
Sterile petri dishes (3)
Sterile gauze
70% ethanol solution
Sterile surgical gloves
20 ml sterile Luer lock syringes (2)
18 G sterile needle
Sterile 50 ml centrifugation tube BD Falcon
40 µm sieve BD ™ Falcon
CS25 OriGen ™ Cryobag
OriGen ™ 25 ml cryobag overwrap
Vacuum Sealer
Cryobag ™ Canister
Sterilin 50 ml sterile beakers (2)

TABLE 1-continued

Sterile Water for Irrigation (saline solution 0.9% NaCl)
Cryo-Labels for donor identity and/or product description
Biosafe Coolmix instrument for automated mixing and cooling to allow the controlled and reproducible preparation of cells for cryopreservation.
Syringe pump
HEPA filtered Laminal Flow Cabinet
20 ml autologous plasma from cord blood processing
For semi automated method: 1) Miltenyi GentleMACS ™ cell dissociation with relevant programs; and 2) Miltenyi C tubes for cellular dissociation/homogenization Responsibilities The LO is responsible to maintain the traceability of UCT throughout processing and the safe banking of the cellular therapy product in the reserved cryostorage location determined at SOP-01 procedures.

The LO is responsible for applying Good Laboratory Practice Manual instructions and work under Good Manufacturing Practice conditions throughout the procedure.

Procedure

The following procedure applies to both automated cell dissociation using GentleMACS™ Technology as well as the manual mincing of the tissue.

Following data verification and acceptance for processing during SOP-01, UCT is transferred to the CLEAN ROOM accompanied by the F-SOP-10/1 and F-SOP-10/2 forms.

The LO shall prepare all components described above and place into the laminal flow cabinet using aseptic techniques.

Remove cord from container using clamps.

Using a sterile gauze, wipe clean the length of the cord

Using scissors cut off the clamped tissue and discard the clamped tissue

Insert the cord in a 50 ml beaker with ethanol for 30 seconds and dry in air. Ensure the clamps are also decontaminated Cut 4 pieces of cord 2.5-3 cm long and place in 50 ml dish containing sterile saline solution For each of the 4 pieces: identify the vein and insert the mosquito clamp all the way to the other end. Identify the 2 arteries. Using the rat tooth trieve clamp one artery and some of its perivascular jelly. Remove the mosquito clamp leaving the vein expanded. Using the other rat tooth trieve clamp on the expanded vein and pull the trieve holding the artery to dissociate the artery and perivascular tissue away from the cord section.

Place the dissociated artery on a petri dish and insert the mosquito clamp to remove the other artery in a similar way described above.

Insert mosquito clamp into the vein. Clamp the Wharton's jelly at the side of the vein with the rat tooth trieve. Remove mosquito clamp and using the other trieve, clamp around the vein.

Holding the vein, pull the trieve holding the jelly to dissociate jelly around the vein. Repeat until vein is fully exposed and cleared of the jelly.

Trim in a similar way the 2 arteries, piling the Wharton's jelly together in the petri dish.

Trimmed vascular system is placed on a petri dish containing saline solution.

Repeat procedure for the other 3 pieces of cord.

Upon completion of the trimming, all Wharton's jelly pieces are chopped into 2-4 mm pieces using scissors.

Weigh the Miltenyi™ C tube and tear the balance. Insert 1.0 g of Wharton's jelly and 1.5 ml of saline or cord blood plasma or both mixed. Choose program C on the Gentle MACS Cell Dissociator™ and run twice (2×).

At the end of the program the dissociated jelly is poured onto a 100 µm sieve standing on a 50 ml Falcon tube. Repeat 4 times until the solution of dissociated cells and plasma reaches 16-17 ml. Wash the sieve with 3-4 ml saline solution until level in Falcon tube reaches 2-21 ml.

Using a 20 ml leuer lock syringe pull the solution, connect to a OriGen™ 20 ml cryobag and transfer the solution into the cryobag.

Proceed to the addition of the cryoprotectant as per SOP-04 for cord blood and sample for bacteriology as per same procedure. Incubate as per MET-04.

Vascular tissue is chopped into pieces similar to wharton's jelly and is dissociated with program C. Pour the solution into a 1.8 ml cryotube cool to 4° C. and pipette 250 µl of DMSO/Dextran solution and mix well. Proceed to gradual rate freezing as per SOP-04 for cord blood sample.

Alternatively, the extracted WJ tissue can be manually minced into a fine "paste" dissolved into 5 ml of autologous plasma in a centrifugation tube, and introduced into a cryobag using a 20 ml syringe.

The cryobag is then weighted and weight recorded on F-SOP-10/1. The LO prepares an appropriate volume of DMSO/Dextran solution in a 20 ml luer lock syringe and proceeds to cryoprotectant administration using the Coolmix instrument. Procedure proceeds as per procedures described in SOP-04 in the same manner to Cord Blood preparation, administration of cryoprotectant, vacuum sealing into an overbag, introduction into Gradual Rate Freezer and eventually to the pre-determined cryostorage location in the liquid nitrogen vessels (banks).

As per SOP-04 a sample of the final product including the DMSO/Dextran solution is cultured for anaerobic and aerobic contamination.

Although the invention has been described with reference to the above examples, it will be understood that modifications and variations are encompassed within the spirit and scope of the invention. Accordingly, the invention is limited only by the following claims.

What is claimed is:

1. A method of isolating mesenchymal cells from umbilical cord tissue comprising:
    a) separating vascular tissue from Wharton's jelly (WJ) matrix from a sample of umbilical cord;
    b) dissociating cells from the WJ matrix in the presence of plasma, sterile saline solution or a combination thereof to form a suspension comprising single dissociated mesenchymal cells;
    c) separating the single dissociated mesenchymal cells from undissociated cells and matrix; and
    d) cryopreserving the separated dissociated mesenchymal cells, thereby isolating mesenchymal cells from umbilical tissue,
    wherein (b) and (c) are performed mechanically and (b) comprises mechanical dissociation via an automated tissue dissociator.

2. The method of claim 1, wherein cryopreserving comprises admixing a cryoprotectant with the separated dissociated cells.

3. The method of claim 1, further comprising verifying that the separated dissociated cells are free of bacterial contaminants.

4. The method of claim 1, wherein (c) is performed by passing the cells through a sieve to remove the undissociated cells and matrix.

5. The method of claim 1, further comprising, prior to (a), clamping the sample thereby preventing the loss of mesenchymal cells.

6. The method of claim 1, wherein (b) is performed in the presence of plasma.

7. The method of claim 1, wherein (b) is performed in the presence of sterile saline solution.

* * * * *